US012678396B2

(12) United States Patent
Seward

(10) Patent No.: US 12,678,396 B2
(45) Date of Patent: Jul. 14, 2026

(54) NATURAL OIL COMPOSITION FOR IMPROVING HAIR GROWTH

(71) Applicant: LaRina Seward, Marietta, GA (US)

(72) Inventor: LaRina Seward, Marietta, GA (US)

( * ) Notice: Subject to any disclaimer, the term of this patent is extended or adjusted under 35 U.S.C. 154(b) by 232 days.

(21) Appl. No.: 18/675,867

(22) Filed: May 28, 2024

(65) Prior Publication Data

US 2025/0009637 A1      Jan. 9, 2025

Related U.S. Application Data

(60) Provisional application No. 63/512,325, filed on Jul. 7, 2023.

(51) Int. Cl.
| | |
|---|---|
| *A61K 8/92* | (2006.01) |
| *A61K 8/9767* | (2017.01) |
| *A61K 8/9789* | (2017.01) |
| *A61K 8/9794* | (2017.01) |
| *A61K 36/15* | (2006.01) |
| *A61K 36/185* | (2006.01) |
| *A61K 36/889* | (2006.01) |
| *A61P 17/14* | (2006.01) |
| *A61Q 7/00* | (2006.01) |

(52) U.S. Cl.
CPC ............ *A61K 8/922* (2013.01); *A61K 8/9767* (2017.08); *A61K 8/9789* (2017.08); *A61K 8/9794* (2017.08); *A61K 36/15* (2013.01); *A61K 36/185* (2013.01); *A61K 36/889* (2013.01); *A61P 17/14* (2018.01); *A61Q 7/00* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 9,636,296 B2 | 5/2017 | Hu | |
| 10,226,495 B2 | 3/2019 | Stottlemyre | |
| 11,185,481 B2 | 11/2021 | Lim | |
| 11,207,511 B2 | 12/2021 | Barman | |
| 2006/0057126 A1 | 3/2006 | Tankovich | |
| 2021/0299023 A1 | 9/2021 | Yoelin | |

FOREIGN PATENT DOCUMENTS

| | | | | | |
|---|---|---|---|---|---|
| CN | 113288853 A | * | 8/2021 | ............. | A61K 8/447 |
| WO | WO-2021152635 A1 | * | 8/2021 | ......... | A61K 36/5775 |

OTHER PUBLICATIONS

Machine translation of CN 113288853 (Aug. 24, 2021).*

* cited by examiner

*Primary Examiner* — John Pak

(74) *Attorney, Agent, or Firm* — Brennan, Manna & Diamond, LLC

(57) ABSTRACT

A hair growth oil composition for promoting hair growth is disclosed. The oil is a unique blend of natural ingredients, comprising 45-55 weight percentage coconut oil, 15-25 weight percentage pine nut oil, 23-30 weight percentage castor oil, and 5-15 weight percentage hibiscus. The oil is applied bi-weekly and the all-natural formula is suitable for sensitive skin, offering a cost-effective, gentle, and accessible alternative to expensive salon treatments and over-the-counter products. In one embodiment, about 6 oz. of coconut oil is mixed with about 2.5 oz. of the pine nut oil to form a mixture. Then, the mixture is tumbled in a mixer device and is mixed with about 2.3 oz. castor oil. The mixing is done at the temperature of about 36° C. and then, about 1 oz. hibiscus is cold pressed and added to form the composition.

16 Claims, 6 Drawing Sheets

Mix 6 oz coconut oil and 2.5 oz pine nut oil to form a first mixture — 202

Tumbling the first mixture and mix with 2.3 oz castor oil — 204

Adding 1 oz hibiscus and storing in different containers — 206

NATURAL OIL COMPOSITION FOR IMPROVING HAIR GROWTH

CROSS-REFERENCE TO RELATED APPLICATION

The present application claims priority to, and the benefit of, U.S. Provisional Application No. 63/512,325, which was filed on Jul. 7, 2023, and is incorporated herein by reference in its entirety.

FIELD OF THE INVENTION

The present invention generally relates to the field of hair oils. More specifically, the present invention relates to a novel hair growth oil composition for improving hair growth The oil is a unique blend of natural ingredients, comprising coconut oil for deep penetration and protein loss reduction, pine nut oil enriched with vitamins E and K, castor oil for hair follicle health, and hibiscus infusion for scalp nourishment. Additionally, essential oils can be added for enhanced scalp health and a pleasant aroma. The oil is applied to the scalp for effective absorption. Accordingly, the present disclosure makes specific reference thereto. Nonetheless, it is to be appreciated that aspects of the present invention are also equally applicable to other like applications, devices, and methods of manufacture.

BACKGROUND

By way of background, hair loss, also known as alopecia, is a very common problem that affects individuals of all ages, genders, and ethnicities. Hair loss can be a source of great emotional distress and can significantly impact the self-confidence and quality of life of a person. Androgenetic alopecia affects both men and women. It is caused by a combination of genetics and hormones. Other types of alopecia such as Alopecia areata, Traction alopecia, and more also affect the hair of individuals. Similarly, hypotrichosis is thinning hair, rather than complete baldness. Overall, hair loss, thinning, and receding hairline can be due to genetic factors, hormonal changes, medical treatments, aging, stress, and more.

Commonly, individuals resort to professional treatments such as provided by specialized salons or clinics for restoring hair growth and improving the health of the scalp. Many individuals use over-the-counter products such as creams, oils, and serums which claim to promote hair growth and strength. Most such products contain harsh chemicals that can potentially worsen hair loss or damage the scalp and hair.

Continuous use of hair growth products can be costly and cannot be accessed by everyone. Further, many conventional treatments and products can have side effects, ranging from scalp irritation to more severe reactions. Some individuals use oils but conventional individual oils are ineffective in promoting hair growth. Individuals end up using different products for eliminating dry hair and scalp, split ends, and breakage which is cumbersome, expensive, and time consuming. Individuals desire a natural and easy-to-use product that can naturally improve hair growth without the use of harsh chemicals.

Therefore, there exists a long-felt need in the art for a novel hair oil designed to improve hair growth. Additionally, there is a long-felt need in the art for a hair growth composition that strengthens hair at the root. Moreover, there is a long-felt need in the art for a hair oil composition that eliminates dry hair and scalp, split ends, and breakage. Further, there is a long-felt need in the art for hair growth composition that contains natural ingredients and does not contain harsh chemicals. Furthermore, there is a long-felt need in the art for a hair growth composition that is cost-effective, natural, and can be used by individuals at home. Also, there is a long-felt need in the art for a natural oil composition for hair growth that functions as a tool for growing and strengthening severely damaged hair. Finally, there is a long-felt need in the art for a hair growth oil that eliminates use of over-the-counter products and expensive hair growth treatments for improving hair quality.

The subject matter disclosed and claimed herein, in one embodiment thereof, comprises a hair growth natural oil composition. The hair growth composition consists of coconut oil, pine nut oil, castor oil, and hibiscus. The hair growth composition is applied to the scalp for effective absorption to promote hair growth and eliminate dry hair and dry scalp. Preferably, the composition is applied twice a week and also includes essential oils for fragrance.

In this manner, the hair growth natural oil composition of the present invention accomplishes all of the foregoing objectives and provides users with a hair care product formulated to improve hair growth, making it particularly beneficial for individuals experiencing thinning or balding hair. The oil is easy to use and can be directly applied to the scalp. The oil has all-natural ingredients, each selected for their unique benefits to hair health and growth. The natural composition of the oil nourishes the scalp without causing irritation. The composition is helpful in hair loss conditions such as alopecia and hypotrichosis.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a hair growth natural oil composition. The hair growth composition consists of coconut oil for deep penetration and protein loss reduction, pine nut oil enriched with vitamins E and K, castor oil for improving hair follicle health, and hibiscus for scalp nourishment. The hair growth composition is applied to the scalp for effective absorption in the scalp to promote hair growth and eliminate dry hair and dry scalp.

In a further embodiment, an oil composition for promoting hair growth is disclosed. The oil composition includes natural ingredients and consists of (i) 45-55 weight percentage coconut oil, (ii) 15-25 weight percentage pine nut oil, (iii) 25-30 weight percentage castor oil, and (iv) 5-15 weight percentage hibiscus.

In yet another embodiment, a hair growth composition in the form of an oil is disclosed. The composition includes 45-65% w/w coconut oil, 18-22% w/w pine nut oil, 23-26% w/w castor oil, 5-12% hibiscus oil and 2-3% w/w essential oil. The composition has the ability to repair follicles, nourish the scalp, and promote hair growth.

In yet another embodiment, a method of making a hair growth composition adapted for promoting hair growth of a human is disclosed. The method comprises the steps of mixing from about 4 oz. to about 8 oz. of coconut oil with from about 1.0 oz. to about 4.0 oz. of pine nut oil to form a mixture. Then, the mixture is tumbled in a mixer device and is mixed with from about 1.0 oz. to about 4.0 oz. castor oil. The mixing is done at a temperature from about 26 degrees C. to about 46 degrees C. and then, from about 0.5 oz. to about 1.5 oz. hibiscus is cold pressed and added to form the composition.

In another aspect, the composition has the viscosity in the range from about 50 to about 80 centipoise (cP) at room temperature.

In another embodiment, the hibiscus is red hibiscus.

In a preferred embodiment, the essential oil is one of rosemary and lavender essential oil.

In another aspect, the composition does not contain any inorganic or synthetic material.

Numerous benefits and advantages of this invention will become apparent to those skilled in the art to which it pertains upon reading and understanding of the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
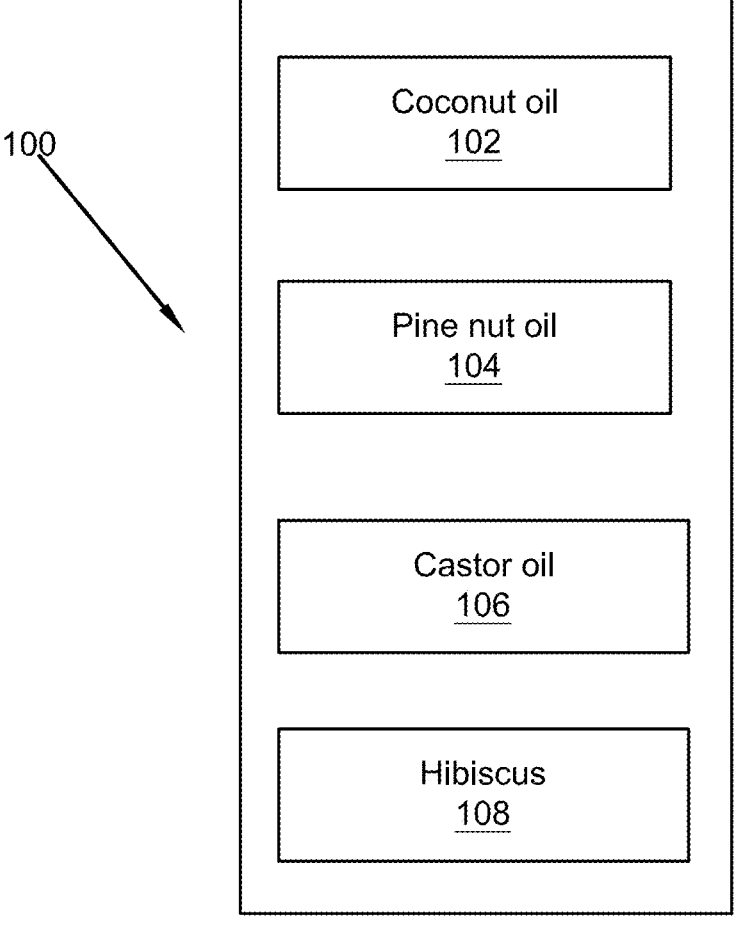
FIG. 1 illustrates a block diagram depicting the ingredients of the hair growth natural oil composition of the present invention, in accordance with one embodiment of the present invention.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for a novel hair oil designed to improve hair growth. Additionally, there is a long-felt need in the art for a hair growth composition that strengthens hair at the root. Moreover, there is a long-felt need in the art for a hair oil composition that eliminates dry hair and scalp, split ends, and breakage. Further, there is a long-felt need in the art for hair growth composition that contains natural ingredients and does not contain harsh chemicals. Furthermore, there is a long-felt need in the art for a hair growth composition that is cost-effective, natural, and can be used by individuals at home. Also, there is a long-felt need in the art for a natural oil composition for hair growth that functions as a tool for growing and strengthening severely damaged hair. Finally, there is a long-felt need in the art for a hair growth oil that eliminates use of over-the-counter products and expensive hair growth treatments for improving hair quality.

The present invention, in one exemplary embodiment, is a method of making a hair growth composition adapted for promoting hair growth of a human is disclosed. The method comprises the steps of mixing from about 4 oz. to about 8 oz. of coconut oil with from about 1.0 oz. to about 4.0 oz. of the pine nut oil to form a mixture. Then, the mixture is tumbled in a mixer device and is mixed with from about 1.0 oz. to about 4.0 oz. castor oil. The mixing is done at a temperature from about 26 degrees C. to about 46 degrees C. and then, from about 0.5 oz. to about 1.5 oz. hibiscus is cold pressed and added to form the composition.

The terms "about" and "approximately" as used herein, indicate that the precision of the nominal value presented is ±7%.

The hair growth oil composition 100 promotes the growth of hair in a subject, in particular, a human subject. Use of the composition 100 results in an increase in the amount or thickness of hair of a subject.

Referring initially to the drawings, FIG. 1 illustrates a block diagram depicting the ingredients of the hair growth natural oil composition of the present invention, in accordance with one embodiment of the present invention.

Table 1 below shows approximate concentrations of various ingredients in the hair growth natural oil composition 100. The hair growth natural oil composition 100 includes coconut oil 102, pine nut oil 104, castor oil 106, and hibiscus 108. The hair growth composition 100 is suitable to help hair grow and eliminate dry hair and scalp. Further, the hair growth composition 100 eliminates split ends and breakage of hair.

The hair growth oil composition 100 is configured to be applied to the scalp of a user and preferably, twice a week. The oil composition 100 is preferably applied overnight but can also be applied about half an hour before a shower. The oil composition 100 includes all-natural ingredients and is designed to optimize hair growth results.

Coconut oil 102 helps to reduce protein loss in both damaged and undamaged hair. Further, coconut oil 102 oil is rich in lauric acid which has a high affinity for hair protein, and easily penetrates inside the hair shaft due to the low molecular weight. Coconut oil 102 helps keep hair strong, nourished, and protected from the effects of premature aging, like thinning and balding.

Pine nut oil 104 is a unique ingredient of the oil composition 100. Pine nut oil 104 provides a high content of vitamins E and K, which promote hair growth and protect against hair loss. Pine nut oil 104 is also rich in antioxidants, which can help to protect the scalp and hair from environmental stressors.

Castor oil 106 improves the health of the hair follicles and promotes hair growth. Castor oil 106 is rich in ricinoleic acid which is a type of fatty acid and fights inflammation. Castor oil 106 also functions as a humectant and moisturizer for improving hair follicle health. The antibacterial and anti-fungal properties of the castor oil 106 reduce dandruff from hair and scalp.

Hibiscus 108 contains vitamins and minerals such as vitamin C, vitamin B6, and iron to help nourish hair, strengthen hair roots, and keep the hair locks lustrous and healthy. Hibiscus 108 has anti-inflammatory properties and also treats issues of the scalp, such as itchiness and dandruff.

TABLE 1

| Ingredients | Composition in percentage by weight (% w/w) |
|---|---|
| Coconut oil | 45-55 |
| Pine nut oil | 15-25 |
| Castor oil | 23-30 |
| Hibiscus | 5-15 |

Coconut oil 102 is the base oil of the composition 100 and prevents the composition 100 from being overly greasy. The pine nut oil 104 is used in a lower percentage than the other two oils 102, 106, due to the vitamin rich nature of the pine nut oil 104. The composition 100 is skin-friendly and does not cause skin irritation, particularly for individuals with sensitive skin.

Table 2 below shows approximate concentrations of various ingredients in another embodiment of the hair growth natural oil composition.

TABLE 2

| Ingredients | Composition in percentage by weight (% w/w) |
|---|---|
| Coconut oil | 45-65 |
| Pine nut oil | 18-22 |
| Castor oil | 23-26 |
| Hibiscus | 5-12 |
| Essential oil (Lavender or Rosemary) | 2-3 |

Essential oils such as lavender or rosemary can be added in some embodiments of the present invention for additional scalp health benefits and a pleasant scent. The concentration of the essential oil is kept under 5% for not overpowering benefits of the core ingredients of the hair growth oil composition 100.

Figure 2:
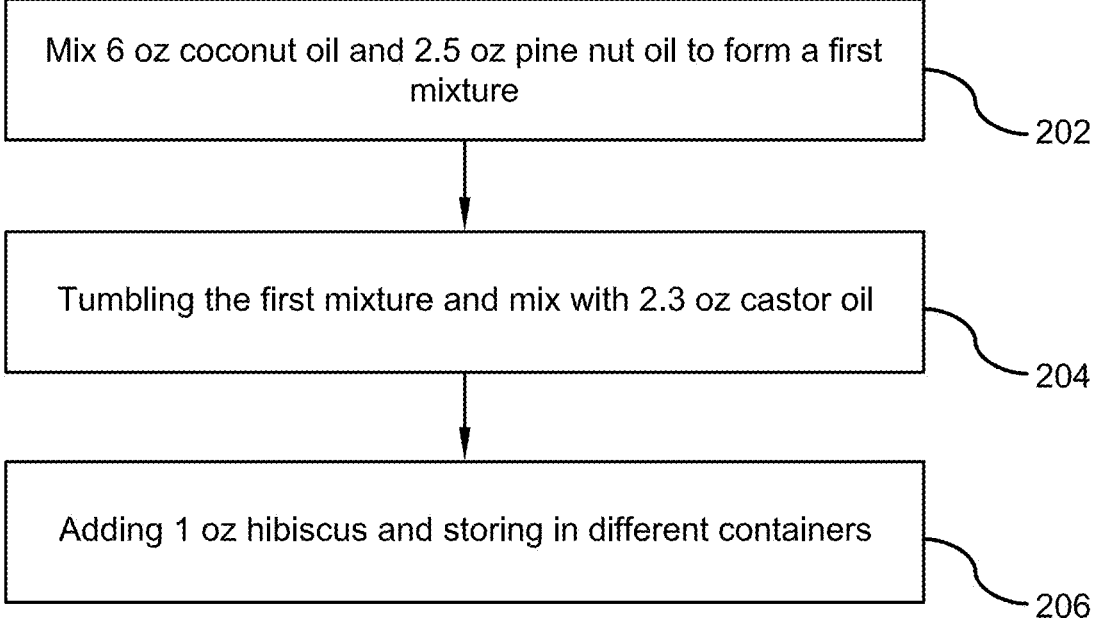
FIG. 2 illustrates the steps performed in making the hair growth natural oil composition of the present invention in accordance with one embodiment of the present invention.

FIG. 2 illustrates the steps performed in making the hair growth natural oil composition 100 of the present invention in accordance with one embodiment of the present invention. The hair growth natural oil composition 100 can be made for both personal and commercial use. For making the composition 100, initially in the step 202, from about 4 oz. to about 8 oz. of coconut oil 102 is mixed with from about 1.0 oz. to about 4.0 oz. of the pine nut oil 104 to form a first mixture. Both the coconut oil 102 and the pine nut oil 104 are cold pressed and organic.

In the next step 204, the first mixture is tumbled in a mixer device and mixed with from about 1.0 oz. to about 4.0 oz. castor oil 106. During mixing of the castor oil 106, the first mixture as made in the above step, and the castor oil 106 are heated to about 26° C. to 46° C. (79° F. to 115° F.) for increasing the efficacy of the oils. Finally, from about 0.5 oz. to about 1.5 oz. hibiscus 108 is cold pressed and added to the mixture of step 204, to form the liquid composition 100 (Step 206) which can be stored in different containers for application on the scalp to promote hair growth.

Figure 3:
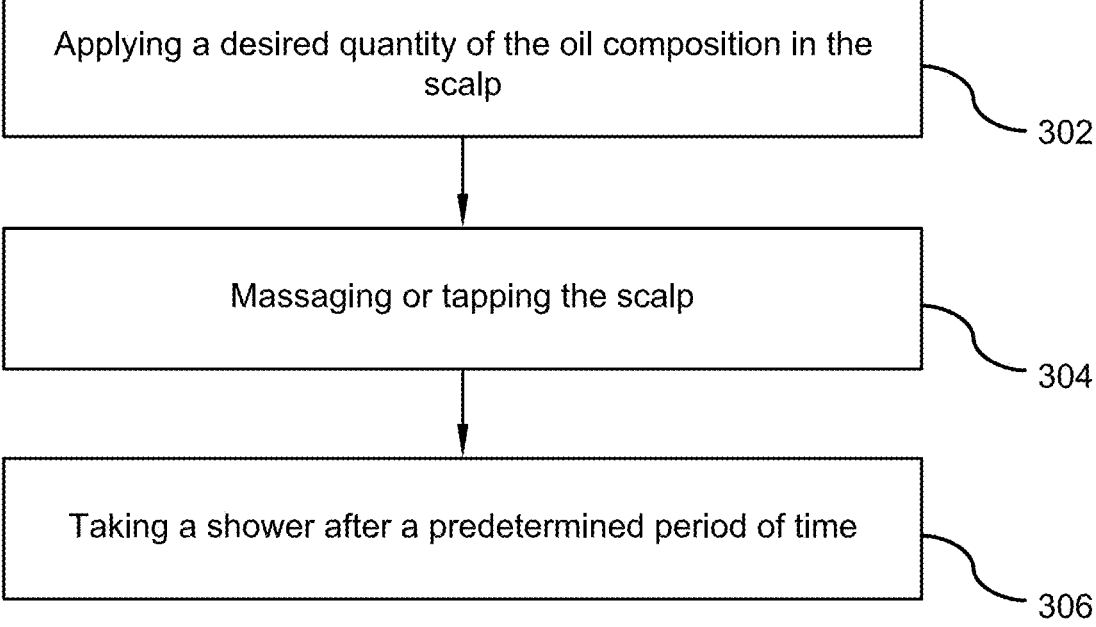
FIG. 3 illustrates the steps performed in using the hair growth oil composition of the present invention in accordance with one embodiment of the present invention.

FIG. 3 illustrates the steps performed in using the hair growth oil composition 100 of the present invention in accordance with one embodiment of the present invention. Initially in step 302, a desired quantity of the composition 100 is applied to the scalp. Then, in step 304, the oil composition applied to the scalp is slightly massaged or tapped for quick and effective absorption. Finally, in step 306, after a predetermined period of time which can range from 0.5 hours to 12 hours, showering can be initiated by the user who had applied the oil composition.

Figure 4:
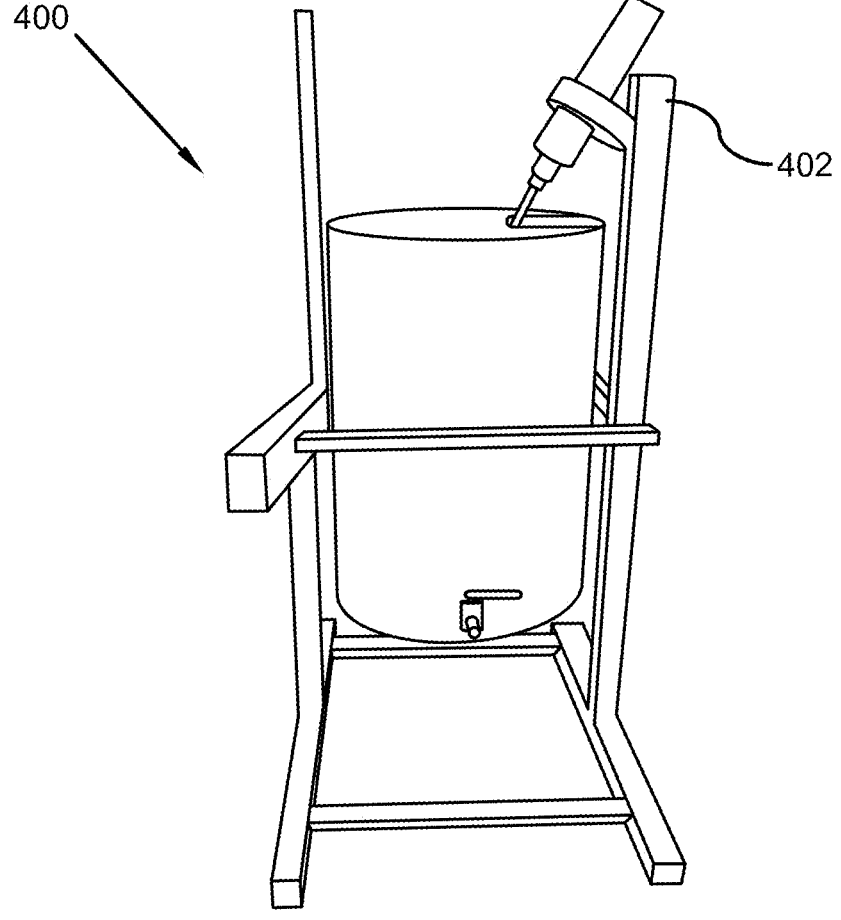
FIG. 4 illustrates an exemplary mixer device used in preparation of the hair growth composition of the present invention in accordance with one embodiment of the present invention.

Referring now to FIG. 4, the mixer device 400 used for forming the composition 100 is illustrated. The mixer device 400 can be of different sizes and shapes and includes a temperature regulator 402 for regulating and warming the oils to make a less greasy composition.

Figure 5:
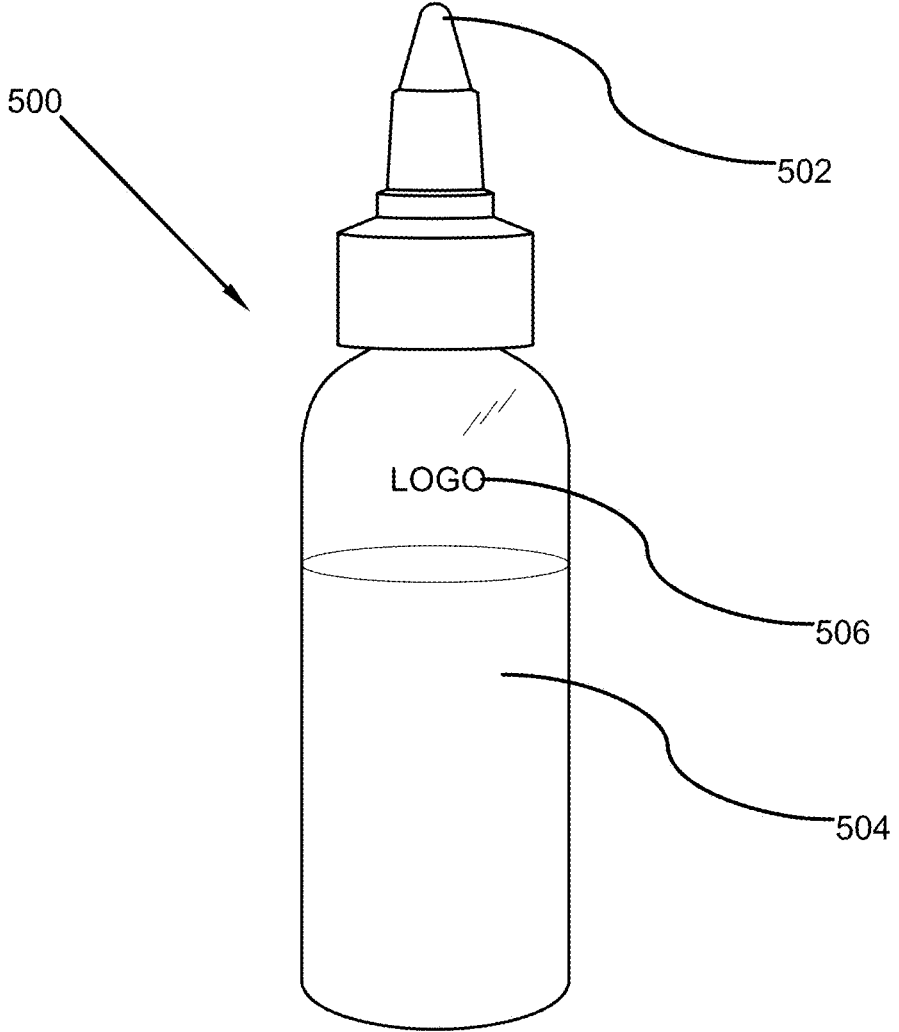
FIG. 5 illustrates an exemplary container for storing and using the hair growth composition of the present invention in accordance with one embodiment of the present invention.

FIG. 5 illustrates an exemplary container for storing and using the hair growth composition of the present invention in accordance with one embodiment of the present invention. The container 500 can come in different sizes and includes a nozzle 502 for dispensing the oil composition 100. The container body 504 can be of different colors and can be made of glass or plastic. A logo or indicia 506 is disposed on the container body 504 for branding and marketing purposes.

Figure 6:
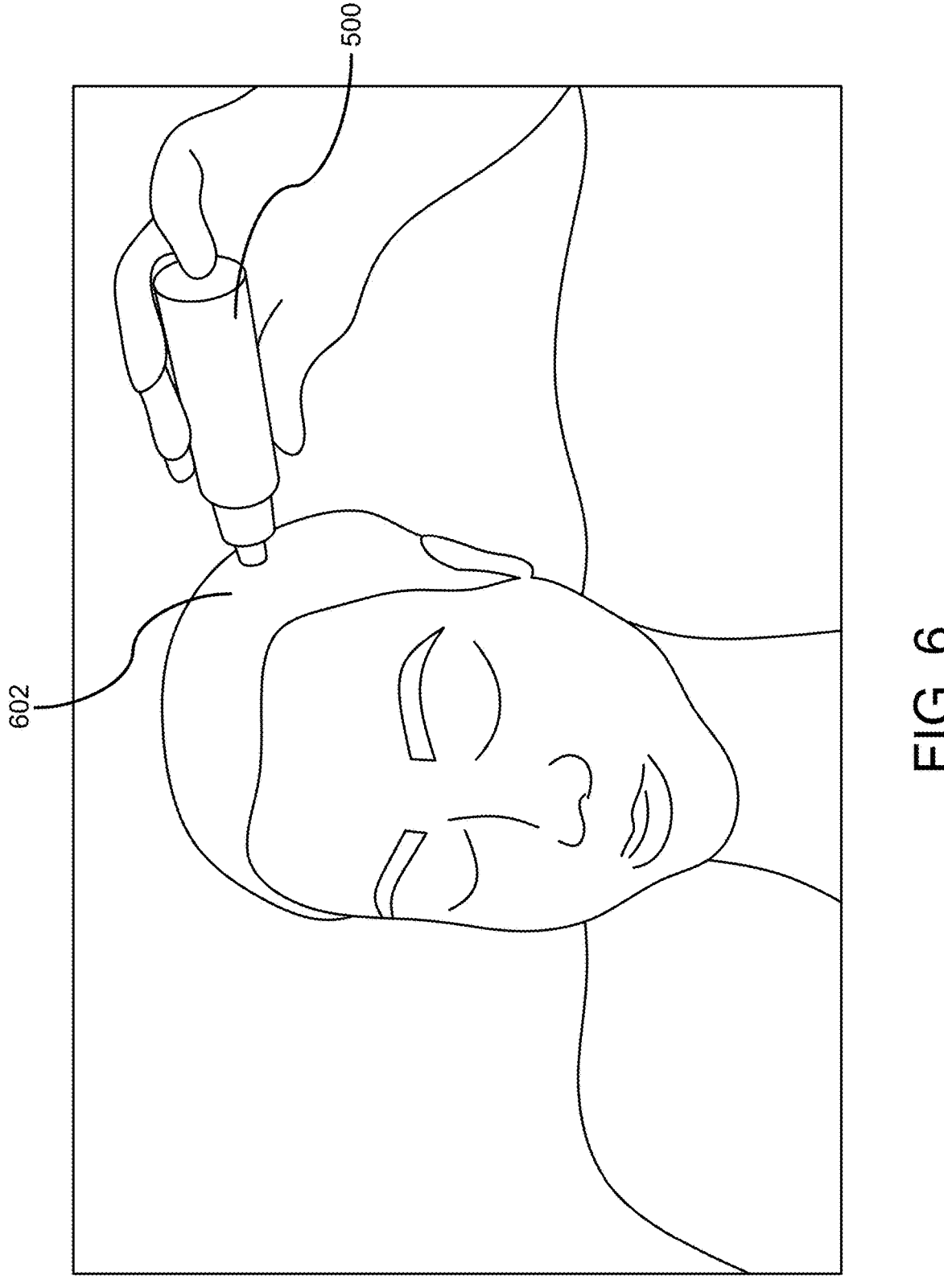
FIG. 6 illustrates a user applying the oil composition for promoting hair growth in accordance with one embodiment of the present invention.

FIG. 6 illustrates a user applying the oil composition for promoting hair growth in accordance with one embodiment of the present invention. The oil composition 100 can be directly applied to the scalp 602 for effective absorption. The composition 100 is easily absorbed in the scalp and does not cause skin irritation. The skin composition 100 offers a simple and convenient method for improving hair quality.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "hair growth natural oil composition", "hair growth oil composition", "oil composition", and "composition" are interchangeable and refer to the hair growth natural oil composition 100 of the present invention.

Notwithstanding the foregoing, the hair growth natural oil composition 100 of the present invention can be of any suitable size and configuration as is known in the art without affecting the overall concept of the invention, provided that it accomplishes the above-stated objectives. One of ordinary skill in the art will appreciate the hair growth natural oil composition 100 as shown in the FIGS. is for illustrative purposes only, and that many other configurations of the hair growth natural oil composition 100 are well within the scope of the present disclosure.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A hair growth composition comprising:
45% w/w to 55% w/w coconut oil;
15% w/w to 25% w/w pine nut oil;
castor oil; and
cold pressed hibiscus oil,
wherein said pine nut oil is present at a lower weight percentage than said castor oil.

2. The hair growth composition of claim 1, wherein said castor oil is present in the composition from 23% w/w to 30% w/w.

3. The hair growth composition of claim 2, wherein said cold pressed hibiscus oil is present in the composition from 5% w/w to 15% w/w.

4. A hair growth composition comprising:
at least 45% w/w coconut oil;
18% w/w to 22% w/w pine nut oil;
castor oil; and
cold pressed hibiscus oil,
wherein said pine nut oil is present at a lower weight percentage than said castor oil.

5. The hair growth composition of claim 4, wherein said castor oil is present in the composition from 23% w/w to 26% w/w.

6. The hair growth composition of claim 5, wherein said cold pressed hibiscus oil is present in the composition from 5% w/w to 12% w/w.

7. A method of making the hair growth composition of claim 4, the method comprising the steps of:
mixing coconut oil, pine nut oil, castor oil, and cold pressed hibiscus oil in amounts effective to provide said hair growth composition.

8. The method of making the hair growth composition of claim 7, wherein said composition comprises 23% w/w to 26% w/w castor oil.

9. The method of making the hair growth composition of claim 8, wherein said composition comprises 5% w/w to 12% w/w cold pressed hibiscus oil.

10. The method of making the hair growth composition of claim 9, further comprising the step of initially mixing said coconut oil with said pine nut oil to form a first mixture.

11. The method of making the hair growth composition of claim 10, further comprising the steps of:
tumbling said first mixture in a mixer device;
adding said castor oil to said first mixture to form a second mixture; and
heating said second mixture to a temperature from 25° C. to 46° C.

12. A method of making a hair growth composition, the method comprising the steps of:
mixing coconut oil, pine nut oil, castor oil, and cold pressed hibiscus oil in amounts effective to provide a hair growth composition comprising:
45% w/w to 55% w/w coconut oil;
15% w/w to 25% w/w pine nut oil;
castor oil; and
cold pressed hibiscus oil,
wherein said pine nut oil is present at a lower weight percentage than said castor oil.

13. The method of making the hair growth composition of claim 12, wherein said composition comprises 23% w/w to 30% w/w castor oil.

14. The method of making the hair growth composition of claim 13, wherein said composition comprises 5% w/w to 15% w/w cold pressed hibiscus oil.

15. The method of making the hair growth composition of claim 14, further comprising the step of initially mixing said coconut oil with said pine nut oil to form a first mixture.

16. The method of making the hair growth composition of claim 15, further comprising the steps of:
tumbling said first mixture in a mixer device;
adding said castor oil to said first mixture to form a second mixture; and
heating said second mixture to a temperature from 25° C. to 46° C.

* * * * *